US006203805B1

(12) United States Patent
Collins et al.

(10) Patent No.: US 6,203,805 B1
(45) **Date of Patent: *Mar. 20, 2001**

(54) TOPICAL COMPOSITIONS CONTAINING WHEY PROTEINS

(75) Inventors: Donald F. Collins, Plainview; Thomas Mammone, Farmingdale; Kenneth D. Marenus, Dix Hills, all of NY (US)

(73) Assignee: Color Access, Inc., Melville, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/189,829

(22) Filed: Nov. 10, 1998

(51) Int. Cl.[7] .............................. A61K 6/00; A61K 7/00

(52) U.S. Cl. .......................... 424/401; 514/844; 514/846; 514/847

(58) Field of Search .......................... 424/401; 514/844, 514/846, 847

(56) References Cited

U.S. PATENT DOCUMENTS

| | | | |
|---|---|---|---|
| 4,223,018 | 9/1980 | Belle . | |
| 5,002,760 | 3/1991 | Katzev | 424/59 |
| 5,386,012 | 1/1995 | Strid . | |
| 5,451,412 | 9/1995 | Bounous et al. . | |
| 5,456,924 | 10/1995 | Bounous et al. . | |
| 5,576,027 * | 11/1996 | Friedman et al. | 424/535 |
| 5,667,791 * | 9/1997 | Hersh et al. | 424/401 |
| 5,690,947 * | 11/1997 | Habif et al. | 424/401 |
| 5,733,884 * | 3/1998 | Barbul et al. | 514/21 |
| 5,747,049 | 5/1998 | Tominaga . | |
| 5,747,538 | 5/1998 | Meybeck et al. . | |
| 5,785,978 * | 7/1998 | Porter et al. | 424/401 |

FOREIGN PATENT DOCUMENTS 58-198409 11/1983 (JP) .

OTHER PUBLICATIONS

Griffiths, C. E. M. et al., "Restoration of Collagen Formation in Photodamaged Human Skin by Tretinoin (Retinoic Acid)", The New England Journal of Medicine, 329, Aug. 19, 1993, pp. 530–535.

Augustin, C. et al., "A Skin Equivalent Model for Cosmetological Trials: An in vitro Efficacy Study of a New Biopeptide", Skin Pharmacol, 10, 1997, pp. 63–70.

Kucharz, E. J., "The Collagens: Biochemistry and Pathophysiology", 1992, pp. 6–29, 79–80, 227–232, Springer–Verlag Heidelberg.

Diminish Retinol Treatment Product Pamphlet and Package Insert (5 pages) publicly available Dec., 1997.

Nutritious Bio–Protein Moisture Complex Product Pamphlet and Package Insert (6 pages) publicly available Dec., 1996.

* cited by examiner

*Primary Examiner*—Thurman K. Page
*Assistant Examiner*—Todd D Ware
(74) *Attorney, Agent, or Firm*—Kenyon & Kenyon

(57) ABSTRACT

The present invention relates to topical compositions comprising a collagen enhancing effective amount of a whey protein, vitamin A, vitamin E and vitamin C in combination with each other. Vitamin E and vitamin C components are present in specific ranges based on their inverse effect in boosting collagen synthesis. The compositions can enhance the production of collagen in skin and improve the resiliency of the skin. The increased production of collagen using the compositions of the present invention restores proteins and vitamins to the skin and helps alleviate some of the effects of aging and photoaging of skin. The present invention also includes methods of applying the compositions to the skin.

17 Claims, 1 Drawing Sheet

TOPICAL COMPOSITIONS CONTAINING WHEY PROTEINS

FIELD OF THE INVENTION

The invention relates to topical compositions containing whey protein which significantly increase the synthesis of collagen in skin. More specifically, the invention relates to topical compositions containing vitamin C, vitamin E and vitamin A in combination with whey protein which have collagen synthesis enhancing properties.

BACKGROUND OF THE INVENTION

Collagen is a fibrous protein that is composed of a triple chain helix structure having a sequence of repeating amino acids, glycine, and X and Y, X and Y being any amino acid, but are usually proline and hydroxyproline. The X and Y amino acids, particularly proline, in addition to the presence of imino acid residues, stabilize the helical structure of collagen.

Collagen constitutes one quarter of the total amount of protein in the human body. It is the major fibrous element of skin, bone, tendons, cartilage, ligaments and blood vessels. Collagen represents about 70% of skin in terms of its dry weight and helps form the structural network of skin. The presence of collagen provides strength and resiliency in skin. While there are various types of collagen throughout the body, the collagen in skin is predominantly Type I and Type III, where 80% to 90% is Type I and the remaining 10% to 15% is Type III. Other types of collagen in skin, for example, Type IV, V, and I trimer are present in considerably smaller amounts.

Collagen is synthesized by fibroblasts. It is believed that as skin ages, the dermis and the epidermis thin because fibroblasts lose their ability to react to growth factors for the proliferation and synthesis of collagen. It has also long been recognized that there is a cause-and-effect relationship between prolonged and/or repeated exposure to UV light and the premature aging of skin. Excessive exposure to the sun contributes substantially to premature reduction in the quality and quantity of collagen in skin. These changes manifest themselves externally by typical signs of aging, such as deep lines and wrinkles, loss of elasticity, skin dryness and unevenness, and increased frequency of blotches, pigmented spots, and benign as well as malignant neoplasms. Kucharz, E. J., "The Collagens: Biochemistry and Pathophysiology", (Springer-Verlag Berlin Heidelberg 1992), pps. 6–29, 79–80, 227–232.

To counteract the undesired effects of both types of aging (i.e., natural and photo-induced), methods of increasing collagen synthesis have been investigated using, for example, a retinoic acid, aminoethyl compound, certain types of growth factors, ginsenoside, ascorbic acid, or tocopherol. See, for example, Kim et al., The Journal of Investigative Dermatology, 98:359–363 (1992); Griffiths, C. E. M. et al., The New England Journal of Medicine, 329: 530–535 (1993); Chojkier et al., The Journal of Biological Chemistry, 264(28):16957–16962 (1989); U.S. Pat. Nos. 5,747,538, 5,747,049 and 5,386,012. In addition, there has been research involving the stimulation of collagen with a peptide. The peptide, in the form of a hydrolysate obtained by fermentation of milk proteins, was found to increase the thickness of the stratum corneum. It did not, however, significantly increase the level of collagen. Augustin et al., Skin Pharmacol 10: 63–70 (1997).

Thus, while various species are known to stimulate collagen synthesis, the topical compositions of the present invention provide a synergistic combination that unexpectedly enhances the stimulation of collagen synthesis. As there is a continued desire to maintain the health of the skin for the purpose of appearing attractive and prolonging a youthful look, a boost in the production of collagen in the skin is important and is the object of the present invention.

SUMMARY OF THE INVENTION

The present invention relates to cosmetic or pharmaceutical compositions containing whey protein for topical application to the skin and methods of enhancing collagen synthesis in the skin. The components of the composition comprise collagen enhancing effective amounts of (a) a retinoid (hereinafter referred to as vitamin A) and derivatives thereof, (b) an ascorbic acid (hereinafter referred to as vitamin C) and derivatives thereof, (c) vitamin E and derivatives thereof, and (d) a whey protein. The vitamins E and C components are present in the composition in specific ranges and the vitamin C component is present in an amount less than the vitamin E component to boost collagen synthesis. Therefore, these compositions are useful in the treatment and prevention of the effects of aging and photoaging, i.e., the damage to the skin which occurs as a result of a decrease in collagen synthesis in skin.

DETAILED DESCRIPTION OF THE INVENTION

Figure 1:
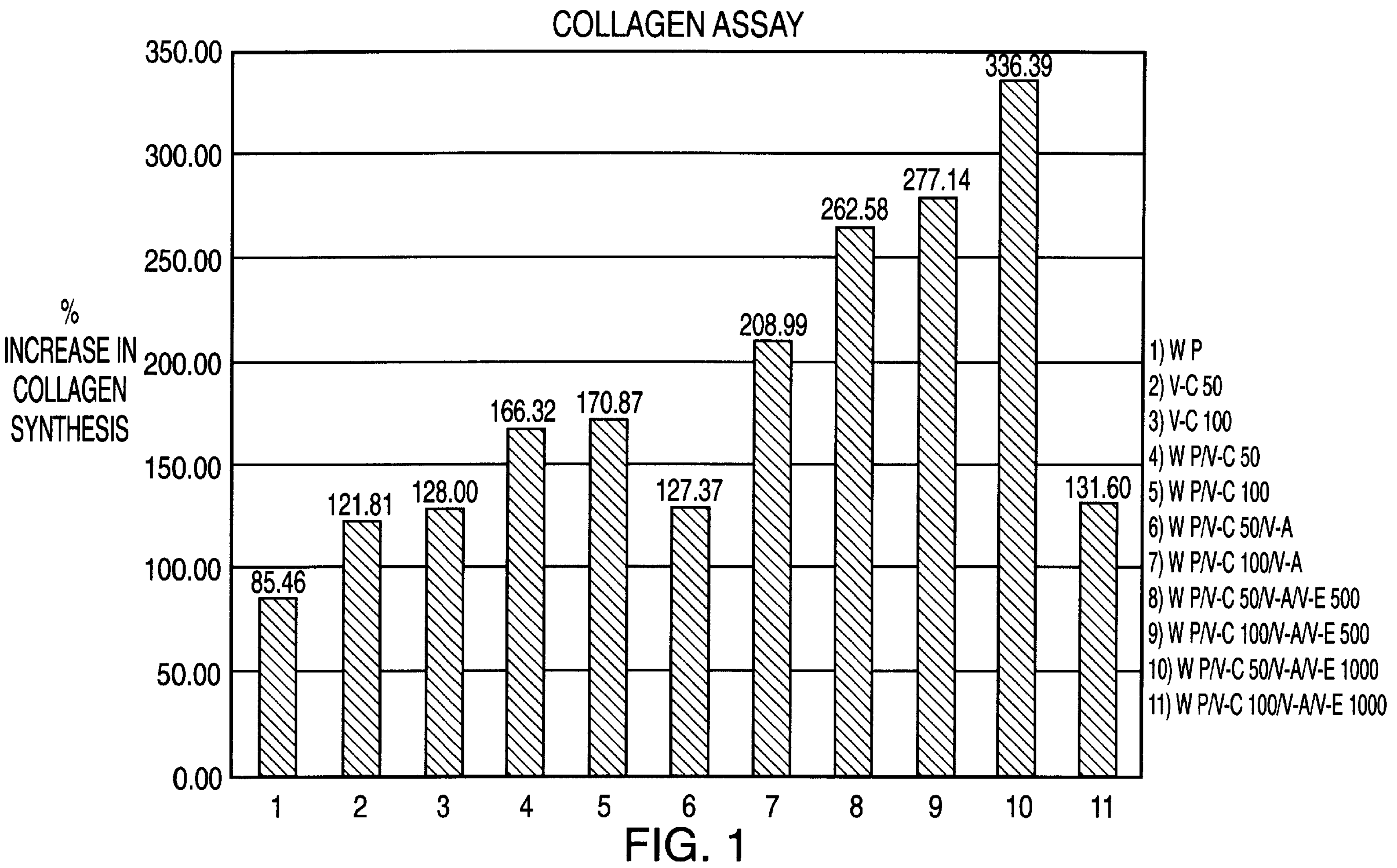
FIG. 1 illustrates the percent increase of collagen production (over media control) in response to the presence of 1) whey protein ("W P"); 2) vitamin C at a low level of 50 μg/ml ("V-C 50"); 3) vitamin C at a high level of 100 μg/ml ("V-C 100"); 4) whey protein with vitamin C at a low level of 50 μg/ml ("W P/V-C 50"); 5) whey protein with vitamin C at a high level of 100 μg/ml ("W P/V-C 100"); 6) whey protein, vitamin A, and vitamin C at a low level of 50 μg/ml ("W P/V-C 50/V-A"); 7) whey protein, vitamin A, and vitamin C at a high level of 100 μg/ml ("W P/V-C 100/V-A"); 8) whey protein, vitamin A, vitamin C at a low level of 50 μg/ml, and vitamin E at a low level of 500 μg/ml ("W P/V-C 50/V-A/V-E 500"); 9) whey protein, vitamin A, vitamin C at a high level of 100 μg/ml, and vitamin E at a low level of 500 μg/ml ("W P/V-C 100/V-A/V-E 500); 10) whey protein, vitamin A, vitamin C at a low level of 50 μg/ml, and vitamin E at a high level of 1000 μg/ml (W P/V-C 50/V-A/V-E 1000"); and 11) whey protein, vitamin A, vitamin C at a high level of 100 μg/ml, and vitamin E at a high level of 1000 μg/ml (W P/V-C 100/V-A/V-E 1000).

When vitamins C and E are combined in specific ranges of amounts with the other essential components (i.e., the whey protein and vitamin A), it is unexpectedly discovered that there is an inverse relationship between quantities specific to vitamin C and vitamin E with respect to increasing the production of collagen. Collagen production is maximized using higher quantities specific to vitamin E and lower quantities specific to vitamin C and conversely, using lower quantities specific to vitamin E and higher quantities specific to vitamin C within certain defined ranges. Therefore, to maximize the collagen synthesis enhancing effect of the compositions, the quantities of vitamins C and E are based on this inverse relationship.

As noted above, it has certainly been recognized that various species are capable of increasing the synthesis of collagen. Various types of compounds, including vitamin A, vitamin E, as well as vitamin C, have been tested to determine if they may have an ameliorating effect on UV-induced damage. Further, while studies in animals have indicated the ability to repair damaged zones in skin due to increased collagen synthesis using vitamin A or vitamin C, results of human studies have been inconsistent in showing that the repair zone was actually due to an increase in collagen synthesis. See Griffiths et al., supra.

It is further known in the prior art to use whey protein for dietary and nutritional purposes as described in U.S. Pat. Nos. 5,451,412 and 5,456,924. For example, it is known to use a combination of milk protein, ascorbic acid, and vitamin A in a composition used for bathing which cleanses and restores vitamins and proteins to the skin as disclosed in U.S. Pat. No. 4,223,018. The use of various compounds alone and/or in combination with each other has increased, however, there is still a lack of understanding of their collective effect on collagen synthesis in skin.

The combination of vitamin C, vitamin E and vitamin A with whey protein, when the vitamin C and vitamin E components are present in specific ranges, have now been unexpectedly shown to be capable of boosting the synthesis of collagen greater than about 300 percent, about three times as much as the same amount of whey protein (e.g., 85 percent increase in collagen synthesis, as shown in FIG. 1, using whey protein alone). A first component of the present invention is the whey protein component. Whey protein, or serum lactis, exists in the supernatant of milk and is the portion of milk left over after butterfat, casein and albumin are removed. Since whey proteins are globular, they are, therefore, water soluble and subject to denaturation which increases their ability to hold water. The primary fractions of whey protein are β-lactoglobulins, α-lactalbumins, bovine serum albumin, and immunoglobulins. The group of β-lactoglobulins accounts for about half of all whey proteins.

In the present invention, the preferred whey protein is denatured and does not contain free amino acids, caseins, casein-bound calcium and phosphate, fat and fat soluble vitamins. The whey protein is denatured by the process of treating milk to make cheese as well as other pasteurization processes such as for example, low pH and high temperature pasteurization methods. In a preferred embodiment of the present invention, the whey protein product is offered commercially under the name VersaPRO E from Davisco International, Inc., Le Sueur, Minn., or similar products may be obtained from other commercial sources.

The other components of the present invention are known materials that are either commercially available or readily prepared. These components are used in collagen enhancing effective amounts. By the term "collagen enhancing effective amount" it is meant an amount which, in combination with the other essential components, enhances collagen production by at least 200 percent, preferably by at least 250 percent, most preferably by at least 300 percent. The collagen enhancing effective amount varies depending upon the identity of the components and their potency. The remaining components are essential to fortifying the effect of the compositions of the present invention as collagen synthesis enhancers.

The first additional component is vitamin A and derivatives thereof. By vitamin A or retinoid in the present context is meant vitamin A (retinol) and any natural or synthetic derivatives, homologs or analogs thereof suitable for use on the skin. Example of retinoids, in addition to retinol include, but are not limited to, retinoic acid (vitamin A acid), retinal (vitamin A aldehyde), and retinoic acid esters or amides, e.g., retinyl palmitate or retinyl acetate.

Another additional component is vitamin E or a homolog, analog or derivative thereof. The principle active component of vitamin E is tocopherol, particularly α-tocopherol; however, any vitamin E or tocopherol derivative may be employed. Examples of useful derivatives include but are not limited to, for example, esters such as tocopherol acetate, tocopherol linoleate, tocopherol nicotinate, tocopherol sorbate, or tocopherol succinate; polyethylene glycol ethers of tocopherol, such as tocophereth-5, tocophereth-10, tocophereth-12, tocophereth-18 or tocophereth-50 and 6-hydroxychroman homologs, particularly 6-hydroxy-2,5,7,8-tetramethylchroman-2-chroman-2-carboxylic acid, commercially available as Trolox®-C and troloxyl-amino acids. The tocopherol derivative may also be a tocopherol-cysteamine or cosmetically or pharmaceutically acceptable salts thereof. The tocopherol-cysteamine compounds can be made using readily available starting materials. It is within the scope of the present invention to use more than one vitamin E component in the mixture, for example, a mixture containing both α-tocopherol and tocopherol cysteamine.

The third essential additional component is vitamin C or a homolog, analog or derivative thereof. Derivatives of vitamin C which may be used include but are not limited to, for example, ascorbyl esters of fatty acids, such as ascorbyl palmitate, ascorbyl dipalmitate, ascorbyl dimethylsilanol palmitate, and ascorbyl stearate, ascorbyl linoleate, ascorbyl acetate; metal or metal phosphate salts, such as magnesium, sodium, or potassium ascorbyl phosphate, or magnesium, sodium or potassium ascorbate.

There is an unexpected increase in collagen synthesis when vitamin E is doubled relative to a standard amount of vitamin E in the presence of the other components (e.g., a combination including 500 μg/ml of vitamin E increases collagen synthesis by about 263% while a combination including 1000 μg/ml of vitamin E increases collagen synthesis by about 336%). The increase in collagen synthesis experienced with the present invention is especially surprising because a combination of about 1000 μg/ml of vitamin E, about 100 μg/ml of vitamin C, about 5 μg/ml of vitamin A and about 1,000 μg/ml of the whey protein (132% increase) is only merely as effective as about 100 μg/ml of vitamin C alone (128% increase) indicating that not all combinations of known collagen enhancers result in a significant additive increase in synthesis. Since increases in vitamin C in combination with other components did not result in an increase in collagen synthesis under the above-mentioned circumstances, it is surprising to discover a composition containing a combination of whey protein, vitamin E, vitamin A, and vitamin C having vitamin C and E in specific ranges that enhances the production of collagen as the present invention does.

Accordingly, in one embodiment of the present invention, the vitamin E component is present in an amount of less than about 800 μg/ml, more preferably less than about 500 μg/ml and the vitamin C component is present in an amount of from about 20 to about 200 μg/ml, more preferably from about 50 to about 100 μg/ml. The vitamin C component is present, however, in an amount less than the vitamin E component. And, in another embodiment of the present invention, the vitamin C component is present in an amount of about 20 μg/ml to about 80 μg/ml, most preferably 20 to 50 μg/ml and the vitamin E component is present in an amount of greater than about 500 μg/ml, preferably greater than about 800 μg/ml, and most preferably greater than 1000 μg/ml.

The whey protein is present in the compositions of the invention in an amount of about 50 to about 10,000 μg/ml, preferably about 750 to about 5,000, and most preferably about 1,000 μg/ml. The vitamin A component is typically present in an amount of from about 1 to about 100 μg/ml, more preferably from about 2 to about 20 μg/ml, and most preferably from about 3.5 to about 5.0 μg/ml.

The whey protein-containing compositions can be combined with a cosmetically and/or pharmaceutically acceptable carrier. The term "pharmaceutically or cosmetically acceptable carrier" refers to a vehicle, for either pharmaceutical or cosmetic use, which vehicle delivers the active components to the intended target and which will not cause harm to humans or other recipient organisms. As used herein, "pharmaceutical" or "cosmetic" will be understood to encompass both human and animal pharmaceuticals or cosmetics. Useful carriers include, for example, water, acetone, ethanol, ethylene glycol, propylene glycol, butane-1,3-diol, isopropyl myristate, isopropyl palmitate, or mineral oil. Methodology and components for formulation of cosmetic and pharmaceutical compositions are well known, and can be found, for example, in Remington's Pharmaceutical Sciences, Eighteenth Edition, A. R. Gennaro, Ed., Mack Publishing Co. Easton Pa., 1990.

The carrier may be in any form appropriate for topical application to the skin, such forms include but are not limited to for example, solutions, colloidal dispersions, emulsions (oil-in-water or water-in-oil), suspensions, creams, lotions, gels, foams, mousses, sprays and the like. The collagen synthesis enhancing compositions can be prepared in any form convenient for topical application to the skin. As will be apparent, the composition can be a therapeutic product, the whey protein, vitamin A component, vitamin E component and vitamin C component being the sole actives.

The compositions of the present invention may also comprise additional useful active ingredients which include, but are not limited to antioxidants, antimicrobials, analgesics, anesthetics, anti-acne agents, antidermatitis agents, antipruritic agents, anti-inflammatory agents, anti-hyperkeratolytic agents, anti-dry skin agents, antiperspirants, antipsoriatic agents, antiseborrheic agents, antiaging agents, antiwrinkle agents, skin lightening agents, depigmenting agents, wound-healing agents, corticosteroids, additional tanning agents, or hormones. The incorporation of the active in the formulation is determined by its solubility and/or stability therein.

The formulation, in addition to the carrier and the essential component mixture, also can comprise other components which may be chosen depending on the carrier and/or the intended use of the formulation. Additional components include, but are not limited to, water soluble colorants (such as FD&C Blue #1); oil soluble colorants (such as D&C Green #6); water soluble sunscreens (such as Eusolex 232); oil soluble sunscreens (such as octyl methoxycinnamate); particulate sunscreens (such as zinc oxide); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/eicosene copolymer); water soluble film-formers (such as hydroxypropyl methylcellulose); oil-soluble film formers (such as hydrogenated C-9 resin); cationic polymers (such as polyquaternium-10); anionic polymers (such as xanthan gum); vitamins; and the like.

The present invention also includes methods of enhancing the synthesis of collagen in skin in which an effective amount of the whey protein-containing compositions is applied to the skin. The compositions of the invention can be applied on an as-needed basis, for example, they can be applied to the skin before anticipated prolonged sun exposure, or during or after such exposure. However, a preferred method of obtaining the benefits of the composition is via chronic topical application of a safe and effective amount of a composition containing the mixture, to prevent the onset of undesirable effects of a reduction in collagen in the skin or the development of skin damage which may occur naturally or may result from exposure to UV light or other environmental insults which may in turn result in the degradation of collagen, or prevent worsening of or reverse existing damage. It is suggested, as an example, that topical application be within a range of from about once per week to about 4 or 5 times daily, preferably from about 3 times a week to about 3 times daily, most preferably about once or twice per day. By "chronic" application, it is meant herein that the period of topical application may be over the lifetime of the user, preferably for a period of at least about one month, more preferably from about three months to about twenty years, more preferably from about six months to about ten years, more preferably still from about one year to about five years, thereby resulting in the treatment or prevention of the external signs of photoaging. It will be recognized by those skilled in the art that the treatment regimen employed can be varied depending upon the user's level of exposure to noxious stimuli; a chronically sun-exposed individual may benefit from more frequent applications than will be necessary for an individual who avoids the sun.

In another embodiment, the composition combines one or more sunscreens with the active components. The combination may be with any sunscreen. Examples of sunscreens useful in the compositions include, but are not limited to, inorganic sunscreens such as titanium and zinc oxides, or organic sunscreens such as para-amino benzoic acid (PABA) and its esters, benzophenones, phenyl or homomenthyl salicylates, and cinnamates. In such a composition, the sunscreen of choice is employed in an amount consistent with the established use of that sunscreen.

The whey protein-containing compositions of the present invention can also be a makeup product, for example, a lipstick, foundation, concealer, bronzer, blush, eyeshadow and the like. Various other optional ingredients may be included with the whey protein-containing compositions of the present invention, these include but are not limited to fragrants, perfumes, flavorings, preservatives, emollients, antiseptics, pigments, dyes, colorants, humectants, propellants, waterproofing agents, film formers, vitamins as well as other classes of materials whose presence may be cosmetically, pharmaceutically, medicinally or otherwise desirable. Common examples can be found in the CTFA International Cosmetic Ingredient Dictionary 4th Edition, The Cosmetic, Toiletry, and Fragrance Association, Inc., Washington, D.C., 1991, the contents of which are incorporated herein.

The invention is further illustrated by the following non-limiting example.

EXAMPLES

I. Preparation of a Whey Protein-containing Composition

The whey protein is prepared by a series of steps. First, whey is produced as a by-product of the manufacturing of cheese and is isolated. The whey supply is initially purified using a clarifier which removes fine pieces or particles of cheese and casein. An additional purification step involves ultrafiltration to separate the whey protein from lactose and other low molecular weight components in the whey. Next, the whey protein is purified by diafiltration. Purified water is used to wash out lactose and minerals. Finally, the whey protein is dried at low temperatures with a high velocity spray dryer. The resulting whey protein is a dry fine white powder.

Vitamins A, C, and E are added in amounts according to the present invention to the appropriate formulation chosen based on its desired use as a product to achieve the additional effect of enhanced collagen synthesis.

II. Collagen Synthesis Activity of Whey Protein and Vitamins A, E and C

Experiments are done examining the effectiveness of the whey protein and vitamin C, individually and various combinations of whey protein, vitamins C, A and E, as collagen synthesis enhancers. The results are illustrated in FIG. 1 and the corresponding resultant numerical data demonstrating the percent increase in collagen synthesis (over media control) is provided in Table 1 below where W P is whey protein, V-C is vitamin C, V-E is vitamin E, and V-A is vitamin A. The numbers after each active component represent the amount of the active component in units of μg/ml. In the absence of vitamin A, changes in levels of vitamin C have little effect on collagen synthesis. This is true for both vitamin C alone and vitamin C in combination with the whey protein (see Table 1, % Increase for Samples 2) V-C 50, 3) V-C 100, 4) W P/V-C 50, and 5) W P/V-C 100 below).

TABLE 1

| Sample | % Increase |
|---|---|
| 1) WP | 85.46 |
| 2) V-C 50 | 121.81 |
| 3) V-C 100 | 128.00 |
| 4) WP/V-C 50 | 166.32 |
| 5) WP/V-C 100 | 170.87 |
| 6) WP/V-C 50/V-A | 127.37 |
| 7) WP/V-C 100/V-A | 208.99 |
| 8) WP/V-C 50/V-A/V-E 500 | 262.58 |
| 9) WP/V-C 100/V-A/V-E 500 | 277.14 |
| 10) WP/V-C 50/V-A/V-E 1000 | 336.39 |
| 11) WP/V-C 100/V-A/V-E 1000 | 131.60 |

It is surprising and unexpected to find that a combination of vitamin A, vitamin C and whey protein and the higher level of vitamin E results in a greater percent increase in production of collagen than vitamin E at the lower level because there is little effect on the level of collagen produced when the amount of vitamin C alone or in combination with the whey protein is doubled from 50 μg/ml to 100 μg/ml. The present invention is most surprising in light of the decrease in collagen synthesis when vitamin C is doubled from 50 μg/ml (336% synthesis) to 100 μg/ml in the presence of vitamin E at the high level of 1000 μg/ml (132% synthesis) and the other components.

A study is done to examine the effect of the combination of vitamin A, vitamin C, vitamin E and whey protein as a collagen synthesis enhancer. The three factors, vitamin A, vitamin C and vitamin E, are tested at high and low levels in a $2^3$ factorial design. For vitamin A, the high and low levels are 5 μg/ml and without; for vitamin C, the high and low levels are 100 and 50 μg/ml; and for vitamin E, the high and low levels are 1,000 and 500 μg/ml. Uniform conditions are maintained with respect to the whey protein which is in an amount of 1,000 μg/ml.

Each treatment combination of the factorial is tested in triplicate. All results are studied using known statistical methods of analysis. Analysis of the results of the designed experiment indicates that vitamin C and vitamin E are main effects and that there is an interaction between them in the presence of vitamin A and whey protein. Within specific ranges of vitamin E and vitamin C, in the presence of vitamin A and the whey protein, an inverse effect as a collagen synthesis enhancer is found.

What we claim is:

1. A topical composition comprising collagen enhancing effective amounts of a whey protein, a retinoid, a vitamin E or derivatives thereof and an ascorbic acid or derivatives thereof, said vitamin E being in an amount of 500 μg/ml or less and said ascorbic acid being in an amount of from about 50 μg/ml to about 100 μg/ml and less than said amount of vitamin E and said retinoid being in an amount of from about 1 μg/ml to about 100 μg/ml.

2. The composition of claim 1 wherein said whey protein is present in an amount of from about 50 μg/ml to about 10,000 μg/ml.

3. The composition of claim 2 wherein said whey protein is present in an amount of from about 750 μg/ml to about 5,000 μg/ml.

4. The composition of claim 1 wherein said retinoid is vitamin A.

5. A collagen enhancing topical composition comprising an amount of vitamin E or derivatives thereof 500 μg/ml or less, an amount of ascorbic acid or derivatives thereof from about 50 to about 100 μg/ml, an amount of whey protein from about 750 to about 5,000 μg/ml, and an amount of retinoid from about 1 to about 100 μg/ml, said amount of ascorbic acid being less than said amount of vitamin E.

6. A topical composition comprising collagen enhancing effective amounts of a whey protein, a retinoid, a vitamin E or derivatives thereof and an ascorbic acid or derivatives thereof, said vitamin E being in an amount of greater than 500 μg/ml and ascorbic acid being in an amount of from about 20 μg/ml to about 50 μg/ml and said retinoid being in an amount of from about 1 μg/ml to about 100 μg/ml.

7. The composition of claim 6 wherein said whey protein is present in an amount of from about 50 μg/ml to about 10,000 μg/ml.

8. The composition of claim 7 wherein said whey protein is present in amount of from about 750 μg/ml to about 5,000 μg/ml.

9. The composition of claim 6 wherein said retinoid is vitamin A.

10. A topical composition comprising an amount of vitamin E or derivatives thereof greater than about 500 μg/ml, an amount of ascorbic acid or derivatives thereof from about 20 to about 50 μg/ml, an amount of whey protein from about 750 to about 5,000 μg/ml, and an amount of retinoid from about 1 to about 100 μg/ml.

11. A collagen enhancing topical composition comprising an amount of vitamin E or derivatives thereof from about 300 to about 800 μg/ml, an amount of ascorbic acid or derivatives thereof of about 50 to 100 μg/ml, an amount of whey protein from about 750 to about 5,000 μg/ml, and an amount of retinoid from about 1 to about 100 μg/ml.

12. A collagen enhancing topical composition comprising an amount of vitamin E or derivatives thereof from about 800 to about 1200 μg/ml, an amount of ascorbic acid or derivatives thereof from about 20 to about 50 μg/ml, an amount of whey protein from about 750 to about 5,000 μg/ml, and an amount of retinoid from about 1 to about 100 μg/ml.

13. A method of enhancing collagen synthesis in the skin comprising applying to the skin a topical composition comprising a collagen enhancing effective amount of a whey protein, vitamin A, vitamin E or derivatives thereof and vitamin C, or derivatives thereof, said vitamin C being present in an amount of about 20 μg/ml to about 50 μg/ml and said vitamin E being present in an amount of from about 500 μg/ml to about 1000 μg/ml and said vitamin A being in an amount of from about 1 μg/ml to about 100 μg/ml.

14. The method of claim 13 wherein the composition comprises from about 50 μg/ml to about 5,000 μg/ml of the whey protein.

15. A method of enhancing collagen synthesis in the skin comprising applying to the skin a topical composition comprising a collagen enchancing effective amount of a whey protein, vitamin A, vitamin E or derivatives thereof, and vitamin C, or derivatives thereof, said vitamin C being present in an amount of about 50 μg/ml to about 100 μg/ml and said vitamin E being present in an amount of about 0 to 500 μg/ml and said vitamin A being in an amount of from about 1 μg/ml to about 100 μg/ml.

16. The method of claim 15 wherein the composition comprises from about 50 μg/ml to about 5,000 μg/ml of the whey protein.

17. A method of enhancing the synthesis of collagen in skin comprising applying to the skin a collagen enhancing effective amount of the composition of claim 1.

* * * * *